US011006620B2

(12) United States Patent
Castellani-Lincontang et al.

(10) Patent No.: US 11,006,620 B2
(45) Date of Patent: May 18, 2021

(54) ANIMAL STUDY MODEL FOR CANCER

(71) Applicants: Universite Claude Bernard Lyon 1, Villeurbanne (FR); Centre National de la Recherche Scientifique, Paris (FR)

(72) Inventors: Valerie Castellani-Lincontang, Villeurbanne (FR); Celine Delloye-Bourgeois, Lyons (FR)

(73) Assignees: UNIVERSITE CLAUDE BERNARD LYON 1, Villeurbanne (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 16/062,417

(22) PCT Filed: Dec. 15, 2016

(86) PCT No.: PCT/EP2016/081316
§ 371 (c)(1),
(2) Date: Jun. 14, 2018

(87) PCT Pub. No.: WO2017/103025
PCT Pub. Date: Jun. 22, 2017

(65) Prior Publication Data
US 2018/0368373 A1 Dec. 27, 2018

(30) Foreign Application Priority Data
Dec. 17, 2015 (FR) ..................... 15 62693

(51) Int. Cl.
*A01K 67/00* (2006.01)
*A01K 67/027* (2006.01)
*C12N 5/073* (2010.01)
*A61K 49/00* (2006.01)
*C12N 5/09* (2010.01)

(52) U.S. Cl.
CPC ...... *A01K 67/0271* (2013.01); *A61K 49/0008* (2013.01); *C12N 5/0604* (2013.01); *A01K 2207/12* (2013.01); *A01K 2207/15* (2013.01); *A01K 2227/30* (2013.01); *A01K 2267/0331* (2013.01); *C12N 5/0693* (2013.01); *G01N 2500/10* (2013.01)

(58) Field of Classification Search
CPC .................................................. A01K 67/0271
USPC ....................................................... 800/8, 19
See application file for complete search history.

(56) References Cited

U.S. PATENT DOCUMENTS 6,228,345 B1   5/2001  Ossowski
2013/0171680 A1 7/2013  Goldstein et al.

FOREIGN PATENT DOCUMENTS

WO   2006/001021 A2   1/2006
WO   2015/074050 A1   5/2015
WO   2016/005398 A1   1/2016

OTHER PUBLICATIONS

Jayachandran (Frontiers in Oncology, 2015, vol. 5, p. 1-7).*
Joel (Developmental Dynamics, 2013, vol. 242, p. 1078-1093).*
Busch (Experimental Dermatology, 2012, vol. 21, No. 12, p. 944-947).*
Hamburger et al: "A series of normal stages in the development of the chick embryo", Journal of Morphology, vol. 88, No. 1, pp. 49-52,Jan. 1951.
Hagedorn et al: "Accessing key steps of human tumor progression in vivo by using an avian embryo model", PNAS, vol. 102, No. 5, pp. 1643-1648, Feb. 1, 2005.
Carter et al: "Exploitation of chick embryo environments to reprogram MYCN-amplified neuroblastoma cells to a benign phenotype, lacking detectable MYCN expression.", Oncogenesis, pp. 1-11, 2012.
Kulesa et al: "Reprogramming metastatic melanoma cells to assume a neural crest cell-like phenotype in an embryonic microenvironment", PNAS, vol. 103, No. 10, pp. 3752-3757 Mar. 7, 2006.
Bouliand et al: "Xenotransplantion of Human Stem Cells into the Chicken Embryo", Journal of Visualized Experiments, vol. 41, pp. 1-6, Jul. 2010.
Jayachandran et al: "Embryonic chicken transplantation is a promising model for studying the invasive behavior of melanoma cells", vol. 5, article 36, pp. 1-7, Feb. 2015.
Ribatti: "The chick embryo chorioallantoic membrane in the study of tumor angiogenesis", Journal of Morphology and Embryology, vol. 49, No. 2, pp. 131-135, 2008.
Bjornstad et al: "Cracking the Egg: Potential of the Developing Chicken as a Model System for Nonclinical Safety Studies of Pharmaceuticals", Journal of Pharmacology and Experimental Therapeutics, vol. 355, No. 3, pp. 386-396, Oct. 1, 2015.
Wan et al: "HIF-1α effects on angiogenic potential in human small cell lung carcinoma", Journal of Experimenta and Clinical Cancer Research, vol. 30, No. 77, pp. 1-14, 2011.
Fujiwara et al: "Therapeutic Effect of a Retroviral Wild-Type p53 Expression Vector in an Orthotopic Lung Cancer Model", Journal of the National Cancer Institute, vol. 86, No. 19, pp. 1458-1462, Oct. 5, 1994.
Meuwissen et al: "Mouse models for human lung cancer", Genes and Development, vol. 19, pp. 643-664, 2005.
Wolfram et al: "Effect of lung flooding and high-intensity focused ultrasound on lung tumors: an experimental study in an ex vivo human cancer model and simulated in vivo tumours in pigs", European Journal of Medical Research, vol. 19, No. 1, pp. 1-9, 2014.
Yan et al: "A novel synthetic compound exerts effective anti-tumour activity in vivo via the inhibition of tubulin polymerisation in A549 cells", Biochemical Pharmacology, vol. 91, pp. 51-61, 2015.
Busch et al: "Human melanoma cells in the rhombencephalon of the chick embryo: a novel model for brain metastasis", Experimental Dermatology, vol. 21, pp. 944-947, 2012.

(Continued)

*Primary Examiner* — Michael C Wilson
(74) *Attorney, Agent, or Firm* — W&C IP

(57) ABSTRACT

The invention concerns a gallinacean embryo in which cancer cells have been grafted within the embryo tissue, characterised in that the embryo is at a developmental stage between the HH10 and HH25 stages at the time of the grafting, wherein said cancer cells are not neuroblastoma cells and said cells form tumors inside the embryo.

18 Claims, 8 Drawing Sheets

(56) References Cited

OTHER PUBLICATIONS

Figure 1:
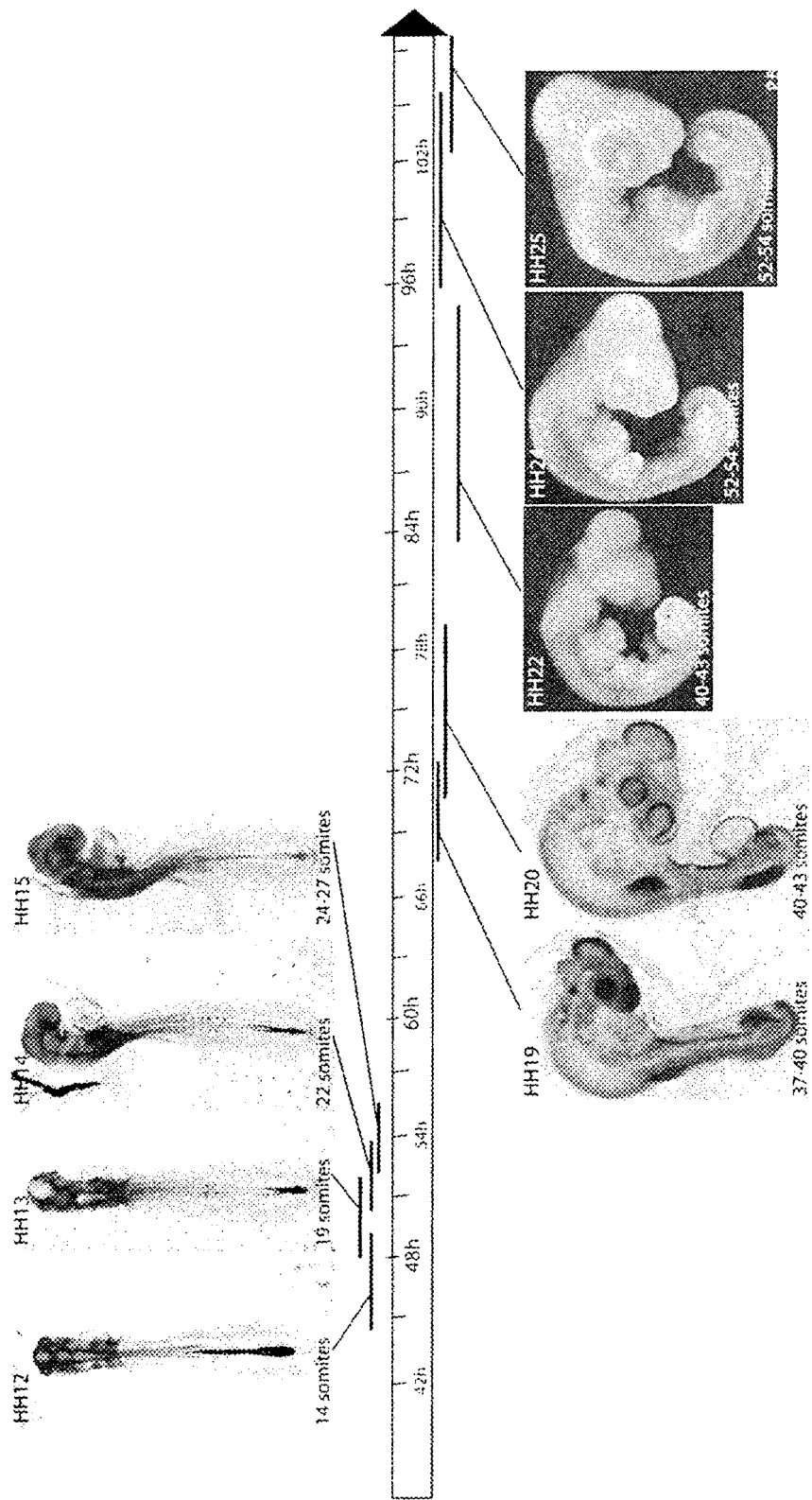

Busch et al: "The Chick Embryo as an Experimental System for Melanoma Cell Invasion", PLOS ONE, vol. 8, issue 1, pp. 2013-01.
Cage et al: "Distinct patterns of human medulloblastoma dissemination in the developing chick embryo nervous system", Clin Exp Metastasis, vol. 29, pp. 371-380, 2012.
Cretu et al: "Human and rat glioma growth, invasion, and vascularization in a novel chick embryo brain tumor model", Clinical & Experimental Metastasis, vol. 22, pp. 225-236, 2005.
Jayachandra et al: "Embryonic chicken transplantation is a promising model for studying the invasive behavior of melanoma cells", Frontiers in Oncology, Molecular and Cellular Oncology, vol. 5, article 36, Feb. 2015.
English Translation of Japanese Office Action, Patent Application No. 2018-531467, dated Aug. 25, 2020.

* cited by examiner

| HH stage | Japanese quail | Chick (Hamburger & Hamilton, 1951) |
|---|---|---|
| 4 | 18–19 h | 18–19 h |
| 5 | 19–22 h | 19–22 h |
| 6 | 23–25 h | 23–25 h |
| 7 | 23–26 h | 23–26 h |
| 8 | 26–29 h | 26–29 h |
| 9 | 29–33 h | 29–33 h |
| 10 | 33–38 h | 33–38 h |
| 11 | 40–45 h | 40–45 h |
| 12 | 45–49 h | 45–49 h |
| 13 | 48–52 h | 48–52 h |
| 14 | 50–53 h | 50–53 h |
| 15 | 50–55 h | 50–55 h |
| 16 | 51–56 h | 51–56 h |
| 17 | 52–64 h | 52–64 h |
| 18 | 72 h | 72 h |
| 19 | 3 days | 3–3.5 days |
| 20 | 3.5 days | 3–3.5 days |
| 21 | 3.5 days | 3.5 days |
| 22 | 4 days | 3.5–4 days |
| 23 | 4 days | 4 days |
| 24 | 4 days | 4 days |
| 25 | 4.5 days | 4.5 days |

Figure 2

A

B

A

B

ANIMAL STUDY MODEL FOR CANCER

FIELD OF THE INVENTION

The present invention relates to an animal model for the study of cancer cells, notably derived from human solid tumours, and more particularly from melanoma, primary and secondary brain tumours, lung tumours and mammary tumours.

INTRODUCTION

The modelling of human cancers in laboratory animals is a central issue in preclinical tests accompanying the development of new anticancer therapies. The major criteria for the animal models developed to that effect are the model's reliability and its speed and cost of execution.

The animal models which have been developed for tumour studies and are in current use are chiefly mouse models. Preparation of these models involves a relatively long execution time and high costs. In addition, certain types of cancer cells cannot be implanted into mouse animal models.

The gallinaceous bird embryo, particularly the chick or quail embryo, is an attractive model for performing ex vivo experiments, in particular for the study of embryonic development and for xenotransplantation experiments. It is indeed inexpensive, very accessible and easy to handle. It is a model of choice for the study of cell proliferation, differentiation and migration. This animal model can also be used to study tumours.

A classic study model using the gallinaceous bird embryo is the grafting of exogenous cells at the extraembryonic structures, more precisely onto the chorio-allantoic membrane (CAM). Tumour cells are implanted on the chick embryo membrane. After incubation for about 2 days, a tumour forms. This tumour takes advantage of the embryonic membrane vasculature, which is particularly developed, in order to grow. Such a system has made it possible to reproduce in vivo human tumours, notably glioblastoma, having cellular and molecular features similar to those observed in the tumours in vivo. (Hagedorn et al., 2005).

These grafts of cancer cells onto the chorio-allantoic membrane have notably been used to determine the metastatic potential of said cancer cells, wherein the grafted cells which cross the membrane are deemed the most likely to metastasize (U.S. Pat. No. 6,228,345).

This chorio-allantoic membrane graft model is also widely used to screen therapeutic molecules, notably molecules for inhibiting tumour angiogenesis (see for example WO 2015/074050).

Patent application US 2013/0171680 describes the xenograft of malignant human hematopoietic cells into other extraembryonic structures: cancer cells are injected into the amniotic sac, the yolk sac, or the blood vessels of the CAM.

Heretofore, little work has been carried out on gallinaceous bird embryo models wherein cancer cells are grafted within the tissues of the embryo and not into the extraembryonic structures thereof.

Carter et al. (Oncogenesis, 2012) injected human neuroblastoma cells into the blood vessels of a chick embryo, between developmental stage days 3 and 6. In contact with the embryonic microenvironment, the cells are reprogrammed to a more benign phenotype, particularly when they integrate into neuronal tissues.

Kulesa et al. (PNAS, 2006) described the transplantation of human melanoma cells into the neural crests of chick embryos at a developmental stage indicated as being "6-8 somites", which corresponds to a stage between HH8.5 and HH9.5 according to the reference nomenclature. At this developmental stage of the embryo, the transplanted cells do not form tumours, are reprogrammed to benign cells and are integrated into tissues following the melanocyte migration pattern.

In these two models, the implanted cancer cells are incapable of reproducing tumours, a fortiori are incapable of reproducing tumours in tissues homologous to those from which said tumours are derived.

Therefore, although the gallinaceous bird embryo is an animal model of choice for the ex vivo study of human tumours, the models developed heretofore do not make it possible to study the migration of cancer cells within a living organism, nor to study tumours in a tissue microenvironment homologous to that of the tumour in vivo.

The present invention relates to the development of an animal model for the study of cancers, notably human cancers, wherein cancer cells grafted within a gallinaceous bird embryo will migrate and create cancer foci in tissues of the embryo corresponding to the tissues from which the cancer cells are derived (orthotopic grafts), or in other tissues (heterotopic grafts).

SUMMARY OF THE INVENTION

The present invention relates to a gallinaceous bird embryo, preferentially a chick or quail embryo, into which cancer cells have been grafted at specific sites within the tissues of the embryo, wherein said cancer cells are not neuroblastoma cells, and wherein said cells form tumours within the embryo.

The grafting is characterized in that it is carried out at a defined point of embryonic development, namely at a point between stages HH10 and HH25, and more specifically between stages HH13 and HH15.

Such a grafted embryo is an animal model for the study of cancers, which makes it possible to follow the migration of the cancer cells and the development of tumours within tissues homologous to the tissues from which the cancer cells originate, and/or where these cancer cells tend to create secondary cancer foci, i.e., tend to metastasize.

Such a grafted embryo is also an animal model for the study of cancers which can implant and/or develop in various tissues of the embryo heterotopically.

Therefore, the present invention relates to a gallinaceous bird embryo into which cancer cells have been grafted within the tissues of the embryo, characterized in that the embryo is at a developmental stage between stage HH10 and stage HH25 at the time of the graft, and wherein said cancer cells are not neuroblastoma cells.

In other words, the present invention relates to a gallinaceous bird embryo comprising at least one tumour consisting of cancer cells which have been grafted within the tissues of the embryo, characterized in that the embryo is at a developmental stage between stage HH10 and stage HH25 at the time of the graft, and wherein said cancer cells are not neuroblastoma cells.

The present invention also relates to a process for preparing a gallinaceous bird embryo into which cancer cells have been grafted and then have formed tumours within said embryo, comprising the following steps:

grafting of cancer cells within the tissues of said embryo, and incubation of the grafted embryo for at least 24 hours, characterized in that the embryo is at a developmental stage between stage HH10 and stage HH25 at the time of the graft, and wherein said cancer cells are not neuroblastoma cells.

The present invention also relates to a process for monitoring a patient with a tumour, comprising:
a) preparation of a first grafted embryo according to the process described above, with cancer cells from said patient at a time $T_1$, and assessment of the tumorigenesis of the tumours developing in this first embryo,
b) preparation of a second grafted embryo according to the process described above, with cancer cells from said patient at a time $T_2$, and assessment of the tumorigenesis of the tumours developing in this second embryo,
c) comparison between the tumorigenesis of the tumours developing in the first grafted embryo and in the second grafted embryo.

The present invention also relates to a process for screening therapeutic molecules intended for the treatment of cancer, consisting of the following steps:
a) preparation of a grafted embryo according to the process described above;
b) administration of a candidate therapeutic molecule to this grafted embryo;
c) assessment of the malignancy of the cancer cells present in this grafted embryo after administration of said candidate molecule.

The present invention also relates to a process for preparing tumours composed of cancer cells, comprising the following steps:
i. grafting of cancer cells within the tissues of a gallinaceous bird embryo at a developmental stage between stage HH10 and stage HH25 at the time of the graft, wherein said cancer cells are not neuroblastoma cells,
ii. incubation of the grafted embryo for at least 24 hours, and
iii. sampling of said tumours formed within the embryo.

These tumours produced in the embryo can be reused as an initial tumour sample, for example for cell cultures, for implantation in another animal model of cancer, or for biochemical and/or molecular biology analyses of said tumours.

FIGURE LEGENDS

FIG. 1. Representation of the early stages of development of the chick embryo, from HH12 (14 somites) to HH25 (52-54 somites).

FIG. 2. Table of correspondence of the early stages of development of the quail (Japanese quail) and chick (chick) embryos as a function of time elapsed since fertilization.

Figure 3:
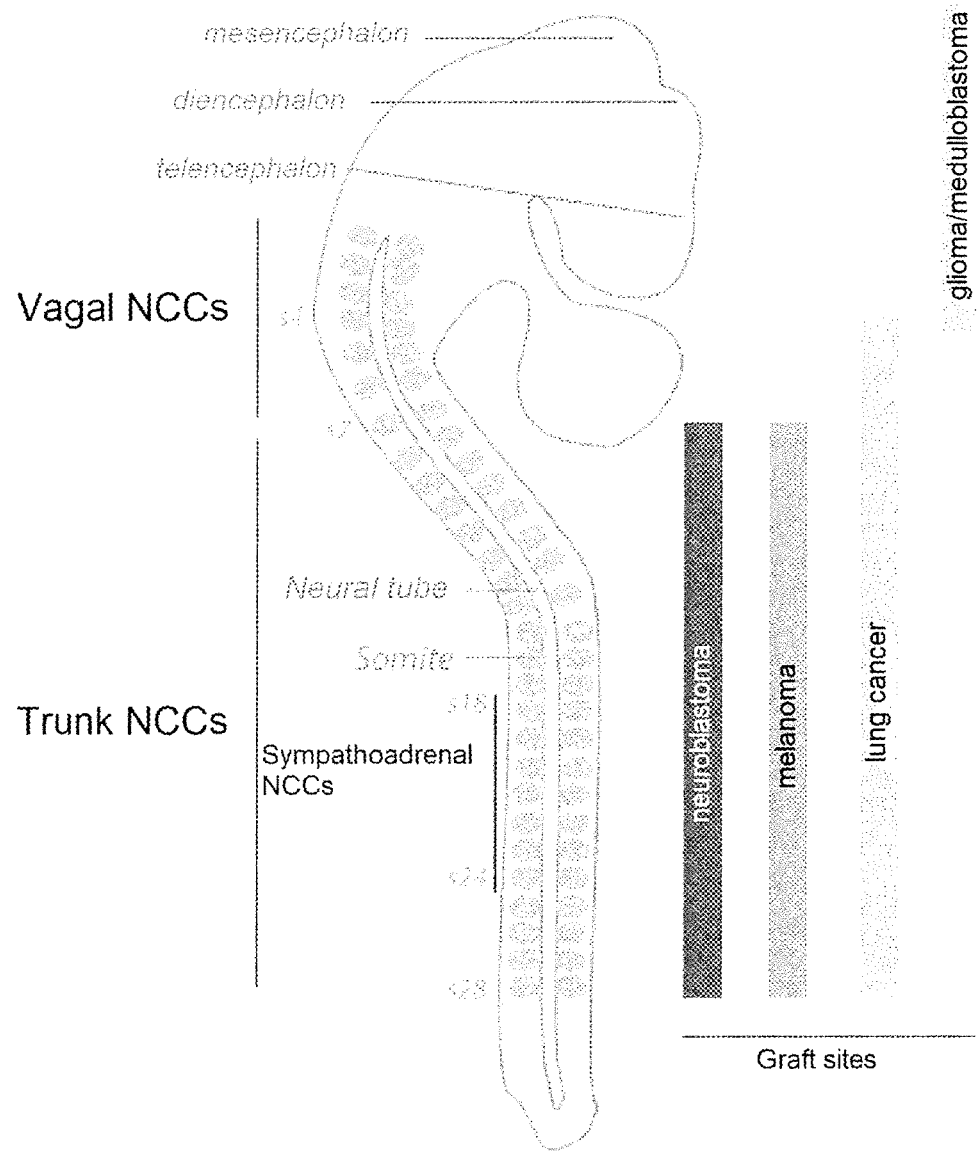

FIG. 3. Longitudinal section of a chick embryo at the 28-somite stage, or stage HH16. The extent of the preferred graft sites, for each cancer cell type, is shown on the right of the figure.

Figure 4:
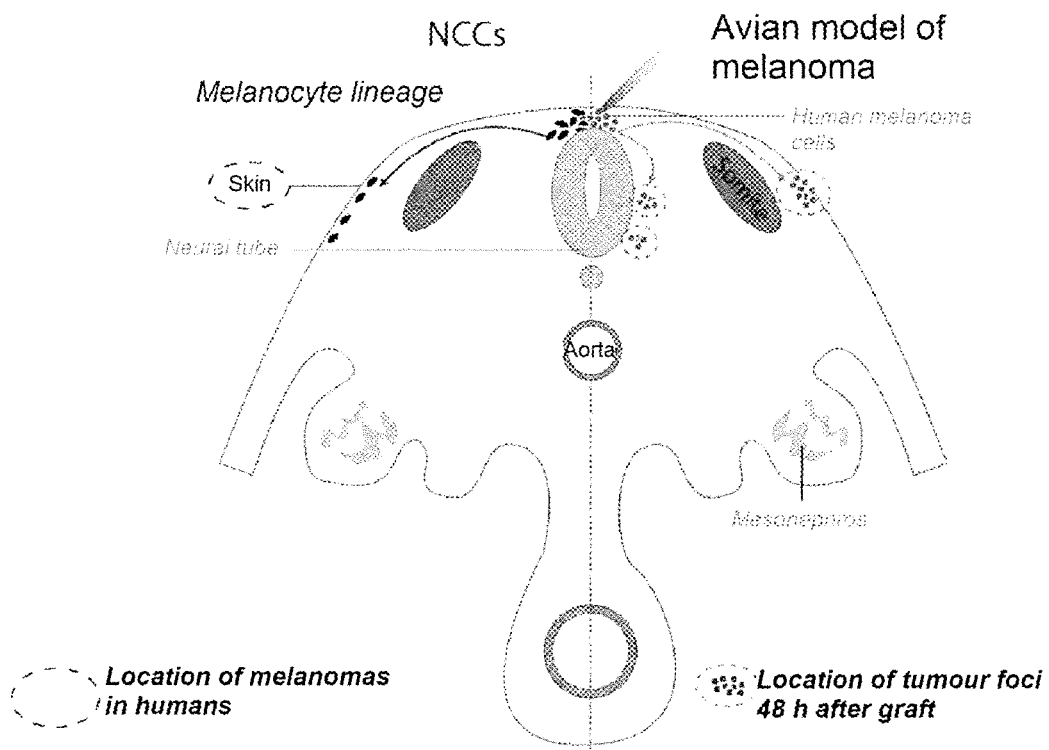

FIG. 4. Cross-section of grafted embryo.
Location of cancer foci 48 h after the grafting of human melanoma cells: the cells grafted into the dorsal roof of the neural tube, between somites 18 to 24, form tumour clusters subcutaneously as well as in the mesenchyme bordering the neural tube (dashed circles).

Figure 5:
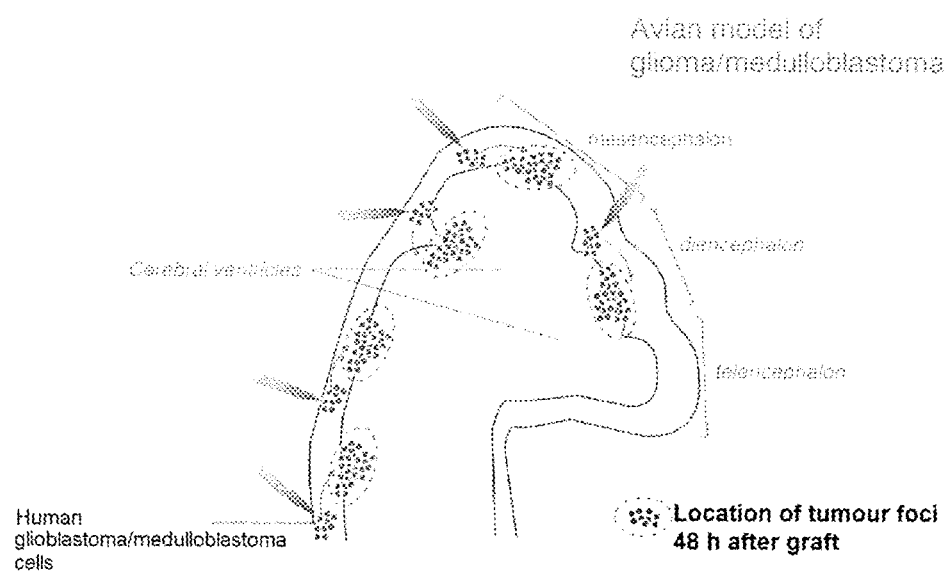

FIG. 5. Longitudinal section of grafted embryo.
Location of cancer foci 48 h after the grafting of human glioma or medulloblastoma cells onto a zone extending from the cervical neural crest (opposite somites 1 to 4) into the tissues bordering the cerebral ventricles of the various brain regions: the grafted cells form tumour clusters in the cerebral tissues.

Figure 6:
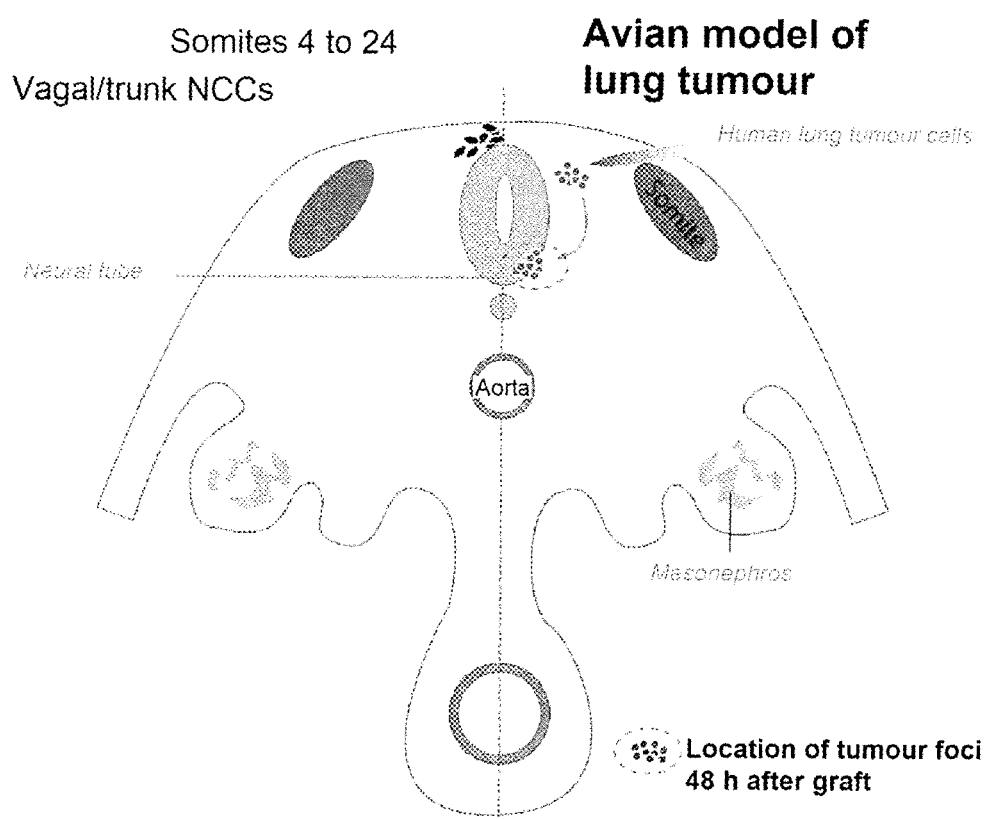

FIG. 6. Cross-section of grafted embryo.
Location of cancer foci 48 h after the grafting of human lung tumour cells: the cells grafted into the lateral mesenchyme opposite the vagal and trunk neural crests (somites 4 to 24) form tumour clusters in the ventral horn of the neural tube and the lateral mesenchyme (dashed circles).

Figure 7:
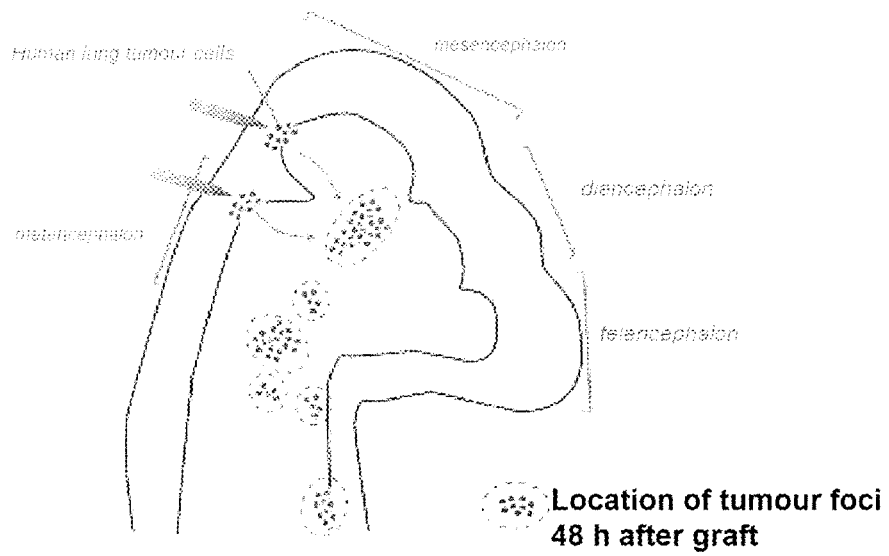
Figure 7:
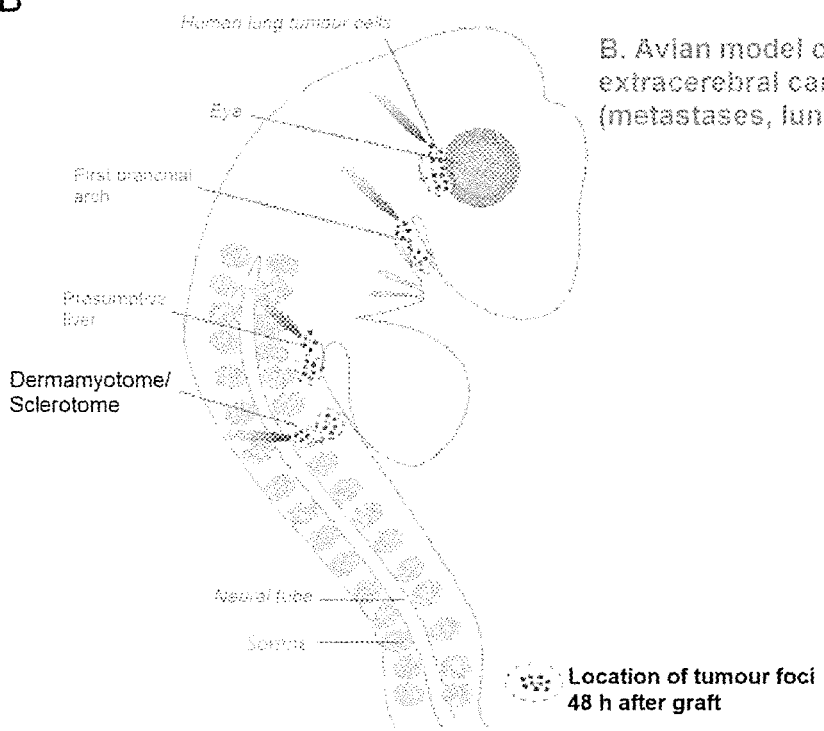

FIG. 7. Longitudinal section of grafted embryo after the grafting of human lung cancer cells.
A. Cerebral location of cancer foci 48 h after the grafting of human lung cancer cells onto a zone extending from the cervical neural crest (opposite somites 1 to 4) into the tissues bordering the cerebral ventricles of the various brain regions: the grafted cells form tumour clusters in the cerebral tissues, similar to cerebral lung metastases in humans.
B. Extracerebral location of cancer foci 48 h after the grafting of human lung cancer cells into zones covering the principal presumptive sites of human lung cancer metastases (periorbital tissue, first branchial arch, hepatic anlage, limb anlage—sclerotome/dermamyotome): the grafted cells form tumour clusters in the cartilage and the bones of the face (periorbital graft and graft into the first branchial arch), in the embryonic liver (graft into the hepatic anlage) and in the tissues deriving from the somites such as the bone tissue (graft into the sclerotome/dermamyotome).

Figure 8:
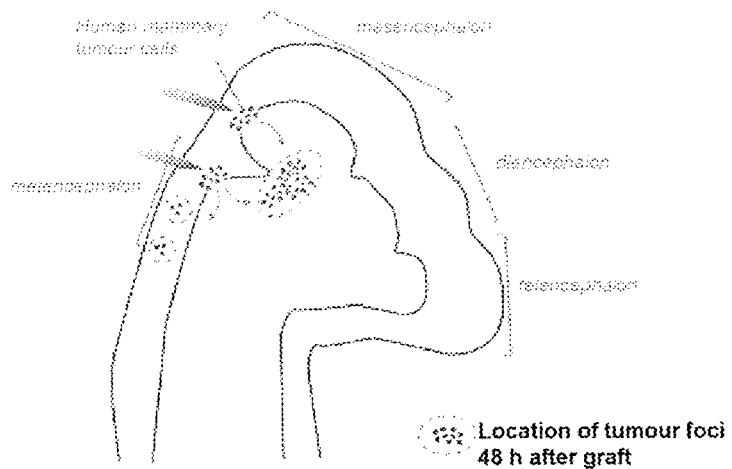
Figure 8:
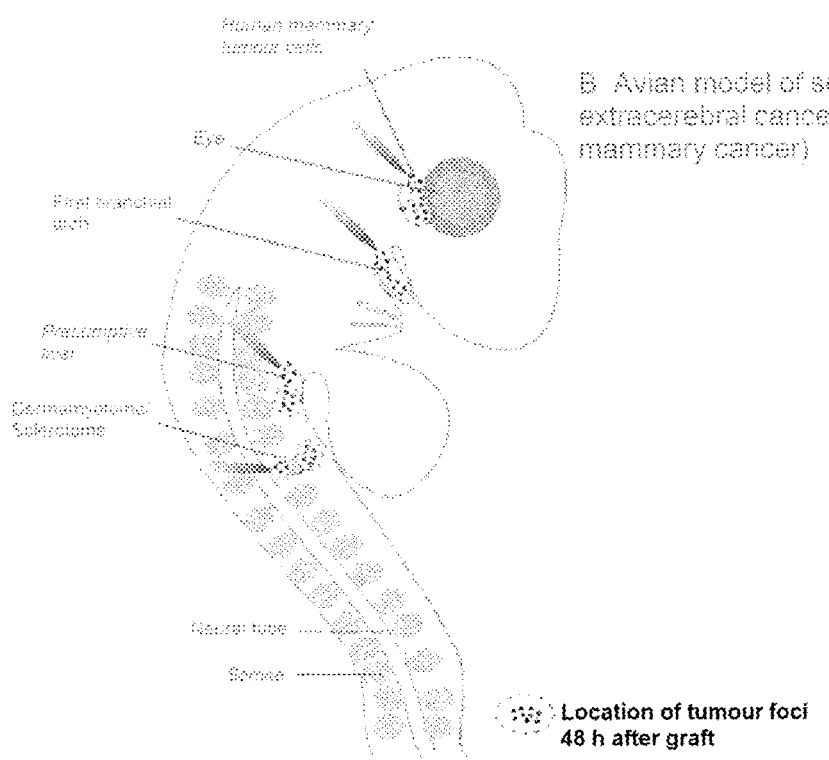

FIG. 8. Longitudinal section of grafted embryo after the grafting of human breast cancer cells.
A. Cerebral location of cancer foci 48 h after the grafting of human breast cancer cells onto a zone extending from the cervical neural crest (opposite somites 1 to 4) into the tissues bordering the cerebral ventricles of the various brain regions: the grafted cells form tumour clusters in the cerebral tissues.
B. Extracerebral location of cancer foci 48 h after the grafting of human breast cancer cells into zones covering the principal presumptive sites of human mammary cancer metastases (periorbital tissue, first branchial arch, hepatic anlage, limb anlage—sclerotome/dermamyotome): the grafted cells form tumour clusters in the cartilage and the bones of the face (periorbital graft and graft into the first branchial arch), in the embryonic liver (graft into the hepatic anlage) and in the tissues deriving from the somites such as the bone tissue (graft into the sclerotome/dermamyotome).

DETAILED DESCRIPTION OF THE INVENTION

The following terms are defined for a better understanding of the invention.

The term "gallinaceous bird" refers a bird of the order Galliformes (or gallinaceans) which includes chicks, quails, turkeys, pheasants, peacocks, guinea fowl, and other farmyard animals. Preferentially, the embryo will be from a chicken (*Gallus gallus*) or from a quail (*Coturnix japonica*), two species commonly used in the laboratory.

The term "gallinaceous bird embryo" refers to a fertilized gallinaceous bird egg in which an embryo develops normally, under suitable conditions, notably by being placed in an incubator heated to a temperature of 37° C. to 39° C. The incubation time needed for the egg to hatch is 21 days.

Within the context of the present invention, the "recipient" or "receptor" embryo is a gallinaceous bird embryo before the grafting step.

Within the context of the present invention, the expression "grafted" embryo or embryo "into which cancer cells have been grafted" refers to a gallinaceous bird embryo after the grafting step, and more particularly refers to the grafted embryo after at least 24 hours of incubation, in which at least one tumour consisting of grafted cancer cells has developed. This grafted embryo, which is the subject-matter of the invention, is an animal model for the study of cancer.

The term "cancer" refers to the pathology characterized by the presence in an organism of malignant cells formed from the transformation, by mutations or genetic instability, of initially normal cells of the organism affected by this pathology.

The expression "grafted embryo" or "embryo into which cancer cells have been grafted" denotes, within the meaning of the invention, a "chimeric embryo", i.e., an embryo possessing cells from at least two different organisms: gallinaceous bird cells and cancer cells from another organism, becoming an integral part of the embryo following their acceptance as graft, and continuing their development by forming one or more solid tumours and/or by continuing to develop according to a mode not regulated by the normal controls of cell division, within the tissues of the recipient gallinaceous bird embryo.

It is understood that the grafted embryo is a chimeric embryo since it comprises two cell types from two different organisms; however, it is not a "chimer" in the strict sense, since the embryo is not intended to develop sufficiently so as to create an adult organism, but is used only to support the cancer cells during a short period of time. In any event, it is understood that this gallinaceous bird embryo will not produce a chimeric living organism, but will be destroyed as soon as the study of the evolution of the grafted cancer cells is completed.

Within the meaning of the invention, the term "grafting" or "transplantation" refers to the introduction of exogenous cells into a recipient organism, within tissues of the embryo.

In particular, this term does not refer to introduction of exogenous cells into the extraembryonic structures, such as the chorio-allantoic membrane, the yolk sac or the amniotic sac. Moreover, this term does not refer to injection of cells into the bloodstream of the embryo.

The present application particularly relates to xenografts, this term referring to the fact that the cells introduced into the recipient embryo are from an organism of a species different from that of the recipient embryo.

The grafting of cancer cells is carried out under suitable conditions allowing said cells to reproduce, to migrate, and to form tumours within the recipient embryo, at relevant sites, either in accordance with their tissue origin or in tissues different from those usually colonized by this cancer cell type.

These "suitable conditions" allow the reproduction, within an animal model, of certain aspects of the disease called 'cancer', and notably the formation of tumours.

These "suitable conditions" are based on the developmental stage of the recipient embryo at the time when the graft is carried out, and on the graft site.

The choice of the graft site notably makes it possible to ascertain the migration of the cancer cells and the implantation thereof in various tissues, to form cancer foci therein. Preferentially, these cancer foci are solid tumours.

Therefore, according to an embodiment of the invention, cancer cells grafted into a tissue (graft site) will be able to migrate in the grafted embryo as a function of this graft site and to implant in a second tissue distinct from the graft site, hereafter called "implantation tissue" or "implantation site", to form at least one tumour. In certain regions, the cells will migrate very locally and implant near the graft site.

Several cases should be considered:

it may be desirable to perform so-called 'orthotopic' grafts corresponding to the establishment of cancer foci in tissues homologous to those in which the cancer cells concerned form primary cancer foci in the organism from which they are derived. These cancer foci may result either from a direct graft into the targeted region or from a graft into a migratory pathway leading the cells into this region. The choice of certain specific graft sites makes it possible to orient such an addressing of the cancer cells towards the implantation tissues, as exemplified in the present application;

it may also be desired to reproduce secondary cancer foci, within tissues in which the cancer cells tend to metastasize; here too, these secondary cancer foci can be obtained by performing either a direct graft into the targeted region, or a graft into a migratory pathway leading the cells into this region, the implantation site;

finally, it may simply be desired to create cancer foci implanting and developing in types of tissues other than those from which the cancer cells originate. These 'heterotopic' grafts correspond to the implantation of a cancer focus in tissue distinct from that which hosts the cancer cells in the organism from which they are derived, whether derived from a primary or a secondary tumour (resulting from metastasis).

Such an animal model thus makes it possible to study both the migration of cancer cells and the implantation thereof within specific tissues, or to study cancer foci formed within heterologous tissues.

The main advantages of this animal model are, in addition to the specificity of the cancer foci implantation sites, its low cost and its speed of preparation.

Moreover, this animal model makes it possible to initiate the development of certain tumours which could be sampled and then transplanted into another animal model, for instance a mouse, or regrafted into the avian embryo, or used to prepare cultures and ex vivo 3D models, or to perform biochemical and molecular analyses.

Developmental Stage of the Recipient Embryo

Several developmental stages of the gallinaceous bird embryo have been defined and are shown in FIGS. 1 and 2. These stages have been defined as a function of post-fertilization incubation time and determined according to the criteria defined by Hamburger and Hamilton (1951, J Morphol.). Furthermore, since somites appear as development progresses, each stage is also characterized by the number of somites present.

It is understood that development of the embryo begins only when the embryo is incubated under suitable conditions, notably at a temperature of 37° C. to 39° C. Therefore, a developmental stage "between 48 and 55 hours" means that the egg has been maintained during this period under the optimal conditions for its development. A fertilized egg can be kept at 14° C. before being placed under optimal conditions for its development; this waiting period at 14° C. is not to be taken into account in the time period indicated below.

According to the invention, at the time of the graft, the gallinaceous bird embryo, particularly the chick or quail embryo, is at a developmental stage between stage HH0 and stage HH25.

Stage HH10 is observed at roughly 33 to 38 hours of incubation, and is characterized by the presence of 10 somites.

Stage HH25 is observed between 102 and 108 hours of incubation, and is characterized by the presence of 52 to 54 somites (see FIG. 1).

Between these two stages, an important event is curvature of the embryo. Indeed, starting with the appearance of the 19$^{th}$ somite (stage HH13), i.e., roughly after 48 hours of post-fertilization incubation, the head of the embryo begins a twisting movement to the left which propagates during organogenesis to the posterior end of the embryo. The progression of this movement is clearly perceptible between 55 and 68 hours of incubation.

Preferably, at the time of the graft, the gallinaceous bird embryo, particularly the chick or quail embryo, is at a developmental stage between stage HH12 and stage HH25, i.e., one of the stages presented in FIG. 1.

This developmental phase of the embryo, taking place between 40 hours and 4.5 days post-fertilization, is characterized by many key events of embryogenesis, among which the appearance of somites, the subdivision of the large brain regions, the curvatures of the various regions of the embryo, and the formation of numerous organs.

According to another preferred aspect, at the time of the graft, the gallinaceous bird embryo, particularly the chick or quail embryo, is at a developmental stage between stage HH10 and stage HH18, between stage HH10 and stage HH15, or between stage HH12 and stage HH16.

Preferably, the grafting of cancer cells is performed on a recipient gallinaceous bird embryo at a developmental stage between stages HH13 and HH15, i.e., between 48 and 55 hours post-fertilization, and preferably between 50 and 53 hours post-fertilization (stage HH14).

At this developmental stage HH13-HH15, the chick or quail embryo comprises between 19 and 27 somites.

Cancer Cells

Within the meaning of the invention, the term "cancer cells" refers to malignant cells, i.e., cells capable of dividing without being subjected to normal controls regulating cell division. Most cancer cells have abnormal features known as 'cytological features of malignancy'.

These cells can form one or more outgrowths equally referred to in the present application as 'tumours', 'neo-tumours', 'tumour foci', 'cancer foci', 'tumour clusters' or 'tumour masses', developing within one or more tissues.

The term "tumour" refers to an excessive cell proliferation leading to a tissue mass having the tendency to persist and to grow, attesting to its biological autonomy. The present invention more particularly relates to malignant tumours. Malignant tumours usually grow rapidly and tend to recur after local eradication. Malignant tumours are poorly delimited, non-encapsulated; their borders are irregular.

Circulating cancer cells, notably blood cells, are characterized by a capacity for anarchic, uncontrolled growth and division.

A living organism having such cancer cells is diagnosed as having cancer.

Within the meaning of the invention, the cancer cells intended to be grafted into tissues of a recipient embryo are from a malignant solid tumour or are hematopoietic cancer cells.

According to a preferred aspect of the invention, they are cancer cells derived from malignant solid tumours.

It is understood that within the meaning of the invention, all cancer cells are concerned, except for neuroblastoma cells.

According to a preferred aspect of the invention, the grafted cancer cells are derived from non-paediatric solid tumours.

According to an aspect of the invention, the grafted cancer cells are derived from human malignant tumours developing in adult individuals.

The invention preferably relates to an animal model intended for the study of human tumours; the cells are therefore preferably human cancer cells. It is nevertheless possible to use the animal model of the invention for the study of non-human animal tumours, notably for the study of tumours developing in mammals other than humans.

According to an aspect of the invention, the grafted cancer cells are selected from the group consisting of: melanoma cells, cells derived from primary or secondary brain tumours, lung cancer cells and breast cancer cells.

They may also be cancer cells selected from HER2+/ER+ mammary tumour cells, prostate cancer cells, sarcoma cells, paediatric glioma cells, and "EGFR-mutant" lung cancer cells.

According to an aspect of the invention, the grafted cancer cells are not melanoma cells.

According to yet another aspect of the invention, the grafted cancer cells are selected from the group consisting of: cells derived from primary or secondary brain tumours, lung cancer cells and breast cancer cells.

For the preparation of the grafted gallinaceous bird embryo, the cancer cells can be grafted in the form of:
- suspended cells, injected into the target tissues;
- a solid piece (block) of tumour tissue;
- an aggregate/homogenate of isolated cancer cells.

The term "graft", as used hereinafter, refers a collection of cancer cells introduced as a group into the recipient embryo.

The grafting of cancer cells into the recipient gallinaceous bird embryo is performed according to the methods well known to persons skilled in the art. The gallinaceous bird embryo is indeed easily accessible, after having made a small opening in the eggshell. In particular, grafting of the cancer cells is performed using a pneumatic microinjector (Picopump PV830, World Precision Instruments). Other techniques for transplanting cells within the gallinaceous bird embryo have been described in the prior art, for example by Kulesa et al. (PNAS, 2006) or by Boulland et al. (JVE, 2010).

According to a preferred embodiment of the invention, the cancer cells are grafted in a quantity of at least roughly 1,000 cells per graft.

Alternatively, the graft comprises a quantity of at least 5,000, 10,000, or 15,000 cancer cells per graft.

According to another alternative, the graft will comprise a quantity of cancer cells ranging from roughly 5,000 to roughly 75,000 cells per graft, from roughly 10,000 to roughly 75,000 cells per graft, or from roughly 15,000 cells to roughly 75,000 cells per graft.

In particular, the graft will comprise roughly 15,000, roughly 20,000, roughly 25,000, roughly 30,000, roughly 35,000, roughly 40,000, roughly 45,000, roughly 50,000, roughly 55,000, roughly 60,000, roughly 65,000, roughly 70,000, or roughly 75,000 cancer cells.

The method for counting the cells is well known to persons skilled in the art. In particular, the number of cells grafted with the microinjector is determined prior to the graft by counting, using a Malassez counting chamber, the number of cells ejected from the capillary tube, during a period of time and at a given pressure.

According to a particular embodiment of the invention, several grafts, each comprising at least 1,000 cancer cells, are transplanted onto a single recipient embryo. In particular, at least two, three, four, five or six grafts are transplanted onto a single recipient embryo, at suitable sites.

According to a preferred embodiment of the invention, the grafted cancer cells are human cancer cells.

According to a particular embodiment of the invention, the grafted cancer cells are human cells derived from a tumour from a patient, i.e., from a human individual with cancer.

The cancer cells have been taken by techniques well known to persons skilled in the art, such as biopsy and microsurgery.

In order to distinguish the cancer cells grafted within the gallinaceous bird embryo, and notably to follow the dispersion and the ability to multiply thereof, the grafted cells are advantageously labelled with a dye or express a marker protein.

Such labelling can be performed using dyes. The cells can in particular be labelled using vital dyes, such as carbocyanides, which have affinity for cell membranes, into which they are incorporated, giving the cells a red fluorescence. Carboxyfluorescein succinimidyl ester (CFSE) dyes, which emit a green fluorescence when reacting with intracellular proteins, can also be used.

According to a particular aspect of the invention, the grafted cancer cells express a marker protein.

A marker protein is a protein encoded by an exogenous gene introduced into the cell by conventional genetic engineering methods, the expression of said gene being under the control of a promoter active in said cell, and said protein being visible, or being capable of reacting with a chemical reagent to become visible. Many marker proteins are known, such as green fluorescent protein (GFP).

Incubation of the Grafted Embryo

Following the graft, the gallinaceous bird embryo is incubated for at least 24 hours according to a standard technique, in a humidity-saturated incubator, at a temperature of 37° C. to 39° C., and preferably of roughly 38.5° C.

As of 24 hours of incubation, the first tumours composed of grafted cancer cells are observed within the grafted embryo.

According to a particular aspect of the invention, the embryo is incubated after the grafting of cancer cells for at least 36 hours, at least 48 hours, at least 60 hours, at least 72 hours, at least 4 days, at least 5 days, at least 6 days, at least 7 days, at least 8 days, and up to 20 days in the case of the study of cancer cells which migrate slowly and/or have a longer kinetics for forming tumours within the grafted embryo.

According to a preferred aspect of the invention, the embryo is incubated for roughly 48 to 52 hours after the graft, preferentially at a temperature of 37° C. to 39° C.

Graft Site

According to a preferred aspect of the invention, cancer cells are grafted into the recipient embryo at the neural tube, between somites 1 and 24, and/or into the brain tissues.

The neural tube comprises the primitive nervous system of embryos. The somites are the embryonic structures located on each side of the neural tube and the cord, and consist of repeating units along the anteroposterior axis of the embryo. At the developmental stage between 48 and 55 hours post-fertilization, i.e., between stages HH13 and HH15, the gallinaceous bird embryo comprises 19 to 27 somites. A representation of the chick embryo at various stages of development, ranging from 14 to 54 somites, is presented in FIG. 1.

Within the meaning of the invention, the expressions "into the neural tube" or "at the neural tube" are synonymous and mean that the cancer cells are introduced within tissues constituting the neural tube, and not in the lumen of the neural tube (which comprises the cerebral ventricles and the central channel of the spinal cord, within which the cerebrospinal fluid circulates).

According to a first aspect of the invention, cancer cells are grafted within tissues constituting the neural tube, between somites 1 and 24.

According to a second aspect of the invention, cancer cells are grafted into the brain tissues. The term "brain tissues" refers to the tissue layers composed of neurons, the zones bordering the ventricles in which neurons arise, the choroid plexus and the external membranes which isolate the brain from the exterior, such as the pia mater and the arachnoid mater.

Brain tissues include the various brain regions such as: telencephalon, diencephalon, mesencephalon, mesenchyme and brain stem.

According to a third aspect of the invention, cancer cells are grafted into the recipient embryo within tissues constituting the neural tube, between somites 1 and 24, and are also grafted into the brain tissues.

According to the present invention, the animal model consisting of a gallinaceous bird embryo grafted with cancer cells is suitable for the study of any cancer cell type. The animal model is however chiefly intended for the study of human malignant solid tumours.

It should be recalled that, within the meaning of the invention, the term "cancer cells" refers to any cancer cell type except for neuroblastoma cells, and includes hematopoietic cancer cells.

According to another aspect of the invention, the term "cancer cells" refers to any cancer cell type except for neuroblastoma cells and melanoma cells, and includes hematopoietic cancer cells.

According to yet another aspect of the invention, the cancer cells are selected from the group consisting of: cells derived from primary or secondary brain tumours, lung cancer cells and breast cancer cells.

For each cancer cell type, the person skilled in the art is able to determine the optimal graft site, in order to direct the migration of the cancer cells towards a tumour development site either appropriate to the cell type concerned or in order to obtain a heterotopic neo-tumour developing in tissues different from those from which the cancer cells originate.

In particular, the cancer cells can be grafted at certain well-defined sites, in order to be "addressed" specifically to certain embryonic tissues, where they will implant and form tumours in tissues equivalent to the tissues from which they come, or into tissues where metastatic secondary tumours tend to appear.

According to an aspect of the invention, cancer cells are grafted into a first tissue distinct from the implantation tissue where the one or more tumours form, the graft into the first tissue directing the grafted cancer cells towards the implantation tissue where they constitute the one or more tumours, i.e., where the one or more tumours develop.

Several cell types have been grafted into a recipient gallinaceous bird embryo, according to the process described in the present application, and notably cancer cells selected from the group consisting of: melanoma cells, cells derived from primary or secondary brain tumours, lung cancer cells and breast cancer cells.

Therefore:

According to a first aspect of the invention, the grafted cancer cells are melanoma cells, and are grafted into the dorsal roof of the neural tube or into the lateral proximity thereof, between somites 18 and 24.

As shown in FIG. 4, this specific graft site makes it possible to obtain, after at least 24 hours of incubation, a grafted embryo where tumours composed of transplanted cells migrate and then develop specifically beneath the skin, thus reproducing the tissue environment of melanoma cells when they are in their initial organism.

Therefore, the grafted cancer cells migrate within the recipient embryo in order to form neo-tumours in tissues equivalent to the human tissues from which they are derived.

According to a second aspect of the invention, the cancer cells are derived from primary or secondary brain tumours, and are grafted into the neural tube between somites 1 and 4, and/or into the brain tissues.

In this particular embodiment, cancer cells derived from primary or secondary brain tumours are grafted into the neural tube between somites 1 and 4, or into the brain tissues within the thickness of the brain tissue or at the border of the cerebral ventricles.

The term "brain tissues" refers to the tissue layers composed of neurons, the zones bordering the ventricles in which neurons arise, the choroid plexus and the external membranes which isolate the brain from the exterior, such as the pia mater and the arachnoid mater.

In a particular embodiment, at least two grafts of cancer cells derived from primary or secondary brain tumours are grafted, one into the neural tube between somites 1 and 4, and the other into the brain tissues.

The expression "primary brain tumours" particularly refers to tumours such as those observed in glioma, glioblastoma or medulloblastoma.

The expression "secondary brain tumour" refers to a tumour formed in the brain, following the spread of metastatic cancer cells derived from a 'primary' tumour. This primary tumour can be found in various organs. The following cancers are those which spread most frequently to the brain: lung, breast, melanoma, kidney, testicular, colorectal, bronchial, lymphoma (especially non-Hodgkin's lymphoma) and leukaemia.

As shown in FIG. 5, these two specific graft sites make it possible to obtain, after at least 24 hours of incubation, a grafted embryo where tumours composed of transplanted cells develop specifically in the brain tissues, thus reproducing the tissue environment of glioma, glioblastoma or medulloblastoma cells, when they are in their initial organism.

According to a third aspect of the invention, the cancer cells are derived from lung tumours and are grafted into the neural tube between somites 4 and 24.

As shown in FIGS. 6 and 7A, this specific graft site makes it possible to obtain, after at least 24 hours of incubation, a grafted embryo where tumours composed of transplanted cells develop specifically in the ventral horn of the neural tube and the adjacent mesenchyme. This formation site, which corresponds to a region of the central nervous system, is an alternative to the formation site of brain metastases. It is thus representative of the implantation of a secondary cancer tumour in the nervous system.

According to a fourth aspect of the invention, the cancer cells are derived from mammary tumours (breast cancer) and are grafted into the neural tube between somites 4 and 24.

As shown in FIG. 7B, this specific graft site makes it possible to obtain, after at least 24 hours of incubation, a grafted embryo where tumours composed of transplanted cells develop specifically in the brain tissues, notably in proximity to the skin layer.

Processes

The present invention also relates to a process for preparing a gallinaceous bird embryo into which cancer cells have been grafted and then have formed tumours within said embryo, comprising the following steps:
grafting of cancer cells within the tissues of a gallinaceous bird embryo, and
incubation of the grafted embryo for at least 24 hours, characterized in that the embryo is at a developmental stage between stage HH10 and stage HH25 at the time of the graft, and wherein said cancer cells are not neuroblastoma cells.

Advantageously, the graft is performed in the neural tube between somites 1 and 24 and/or in the brain tissues.

Advantageously, the grafted embryo is incubated for roughly 48 to 52 hours after the graft, at a temperature of 37° C. to 39° C.

Advantageously, the cancer cells are derived from a tumour taken from a patient, and are grafted in a quantity of at least 1,000 cells/graft.

Advantageously, the graft is performed according to the particular conditions detailed above.

The present invention also relates to a process for monitoring a cancer patient, comprising:
a) preparation of a first grafted embryo according to the process described above, with cancer cells from said patient at a time $T_1$, and assessment of the malignancy index of the cancer cells developing in this first embryo,
b) preparation of a second grafted embryo according to the process described above, with cancer cells from said patient at a time $T_2$, and assessment of the malignancy index of the cancer cells developing in this second embryo,
c) comparison between the malignancy index of the cancer cells developing in the first embryo and the second embryo.

"Assessment of the malignancy index" is performed by several complementary approaches; after sampling of the cancer cells developing in the grafted embryo, they are subjected to various analyses:
biochemical and transcriptomic studies, and
in vitro studies via the reculturing thereof.

These various analyses make it possible in particular to determine the malignancy index relative to the following factors:
Determination of the proliferation index of the cancer cells by detection of marker Ki67;
Determination of the cell death index of the cells by detection of cell death events (DNA fragmentation, necrosis, cytochrome c release, pro-apoptotic protease activation)
Analysis of the transcriptome and of the proteome of the cells;
Study of the cell behaviour after reculturing.

The combined analysis of all these factors, well known to persons skilled in the art, makes it possible to determine a 'malignancy index' allowing quantification of the seriousness and the aggressiveness of the cancer. Indeed, all these parameters allow evaluation of the state of differentiation of the cancer cells and also the capacity thereof to proliferate and to spread in the organism. These parameters are an integral part of the anatomopathological classification of cancer cells which clinicians use as a basis for directing therapeutic management.

The present invention also relates to a process for monitoring a patient with a tumour, notably a malignant solid tumour, comprising:

a) preparation of a first grafted embryo according to the process described above, with cancer cells from said patient at a time $T_1$, and assessment of the tumorigenesis of the tumours developing in this first embryo, b) preparation of a second grafted embryo according to the process described above, with cancer cells from said patient at a time $T_2$, and assessment of the tumorigenesis of the tumours developing in this second embryo, c) comparison between the tumorigenesis of the tumours developing in the first embryo and the second embryo.

The expression "patient with a tumour" refers to a human being suffering from cancer and having a solid tumour on a given organ.

"Assessment of the tumorigenesis of the tumours" is performed by several complementary approaches; after sampling of the tumours appearing in the grafted embryo by microdissection, they are subjected to various analyses:

biochemical and transcriptomic studies, and in vitro studies via the reculturing thereof.

These various analyses make it possible in particular to determine the following "tumorigenesis factors":

Location of the tumour foci by histological analysis;

Measurement of the tumour volume from 3-dimensional reconstructed images;

Determination of the proliferation index within the tumour foci by detection of marker Ki67;

Determination of the vascularization index of the tumour foci by detection of markers of angiogenesis;

Determination of the cell death index within the tumour foci by detection of cell death events (DNA fragmentation, necrosis, cytochrome c release, pro-apoptotic protease activation)

Analysis of the transcriptome and of the proteome of the tumours extracted in situ;

Study of the cell behaviour after reculturing.

The combined analysis of all these factors, well known to persons skilled in the art, makes it possible to determine a 'tumorigenesis index' allowing quantification of the seriousness and the aggressiveness of the tumour. Indeed, all these parameters allow evaluation of the state of differentiation of the cancer cells and also the capacity thereof to proliferate and to spread in the organism. These parameters are an integral part of the anatomopathological classification of tumours which clinicians use as a basis for directing therapeutic management.

Therefore, it is possible to distinguish:

tumours which develop following the graft, in a gallinaceous bird embryo, of cancer cells from a patient at a time $T_1$, and tumours which develop following the graft, in a gallinaceous bird embryo, of cancer cells from a patient at a time $T_2$.

Such a process makes it possible to monitor, ex vivo, the development of the patient's solid tumour, and in particular the tumorigenesis index of their cancer cells at a time $T_0$ (e.g., before the beginning of a treatment) and at a time $T_1$, $T_2$, $T_3$ (e.g., several months after the beginning of the patient's treatment).

The process may naturally be repeated the number of times required to monitor the progression of the tumour in a given patient.

The present invention also relates to a process for screening therapeutic molecules intended for the treatment of cancer, consisting of the following steps:

a) preparation of a grafted embryo according to the process described above;

b) administration to this embryo of a candidate therapeutic molecule;

c) assessment of the malignancy of the cancer cells present in this embryo after administration of said candidate molecule.

The term "candidate therapeutic molecule" refers to a chemical or biological molecule that is potentially efficacious for treating the cancer concerned.

Step b) can be performed in several ways: the molecule can be administered to the embryo before or after the grafting of cancer cells has been performed. In particular, the therapeutic molecule can be injected into the vasculature of the embryo, can be incorporated into the yolk sac, or can be used on the graft before or at the time the grafting is performed.

According to this aspect of the invention, the cancer cells intended to be grafted onto the recipient embryo are incubated with a therapeutic molecule before/during grafting onto the recipient embryo.

Assessment of the malignancy of the cancer cells is performed by the approaches described above, after sampling of the cancer cells developing in the grafted embryo. Comparison of the malignancy of the cancer cells at time $T_0$ and of the cancer cells after at least 24 hours, and in particular after 1 ($T_1$), 2 ($T_2$) or 3 ($T_3$) days of administration of the molecule tested, makes it possible to determine the effect of the therapeutic molecule administered.

Naturally, the administration of this molecule can be carried out for various lengths of time, notably for at least 24 h, 48 h, 72 h, 96 h, and up to 5 days, 6 days, 7 days, 8 days, 9 days, 10 days, 11 days, 12 days, 13 days, 14 days, 15 days, 16 days, 17 days, 18 days, 19 days, 20 days, 21 days or up to the hatching of the egg, provided that the tumours are still present in the gallinaceous bird embryo.

It is understood that after the various tests are performed, the embryo is sacrificed according to the ethical rules in force.

The present invention also relates to the use of a gallinaceous bird embryo according to the invention, in order to allow the development of tumours composed of cancer cells.

In particular, it is possible to obtain the in vivo development of tumours composed of cancer cells in the gallinaceous bird embryo according to the invention, whereas these cancer cells have difficulties implanting and forming tumours in mammalian animal models, for instance in mice.

In particular, it has been observed that the following cancer cells have difficulty implanting, after a graft in mammalian animal tissues: liver cancer cells, prostate cancer cells, and cells derived from low-proliferative cancers such as HER2+/ER+ mammary tumour cells, sarcoma cells and paediatric brain tumour cells.

The present animal model advantageously allows the development of tumours composed of cancer cells, said cancer cells generally having difficulties implanting after being grafted into a mammalian animal model.

The present invention thus relates to a process for preparing tumours composed of cancer cells, comprising the following steps:

grafting of cancer cells within the tissues of a gallinaceous bird embryo at a developmental stage between stage HH100 and stage HH25 at the time of the graft, and wherein said cancer cells are not neuroblastoma cells, incubation of the grafted embryo for at least 24 hours, and sampling of said tumours formed within the embryo.

The tumours thus sampled may then be used as would an initial tumour sample, for example for the preparation of cell cultures, to be implanted into another animal model, or for performing biochemical and/or molecular biology analyses of said tumours.

According to an embodiment of this process of the invention, the grafted cancer cells are neither neuroblastoma cells nor melanoma cells.

According to yet another embodiment of the process of the invention, the grafted cancer cells are selected from the group consisting of: cells derived from primary or secondary brain tumours, lung cancer cells and breast cancer cells.

According to yet another embodiment of the process of the invention, the grafted cancer cells are selected from: HER2+/ER+ mammary tumour cells, prostate cancer cells, sarcoma cells, paediatric glioma cells, and "EGFR-mutant" lung cancer cells.

As indicated above, it is understood that after the various processes according to the invention are performed, the gallinaceous bird embryo is sacrificed according to the ethical rules in force.

EXAMPLES

The sole purpose of the examples below is to illustrate the invention, and in no case limit the invention to the particular embodiments described below.

MATERIALS AND METHODS

Human Cancer Cell Lines

Human lung cancer (line A549), melanoma (line A375P), glioblastoma (line U251), medulloblastoma (line DEV) and breast cancer (line MDA MB 436) cells were genetically manipulated to stably express green fluorescent protein (GFP).

Chick Embryos

Fertilized chicken (*Gallus gallus*) eggs were purchased from a supplier (EARL Morizeau, Dangers, France) and kept at 14° C. until use. The eggs were incubated at 38.5° C. for 52 hours in a saturated-humidity incubator so as to obtain embryos at developmental stage HH14.

Human Cancer Line Grafts in the Chick Embryo $5 \times 10^6$ cancer cells were harvested and then resuspended in 30 µL of medium.

After 52 hours of incubation at 38.5° C., a window was cut in the shell in order to visualize and access the embryo. The vitelline membrane was cut at the neural tube and a wound was made in the roof of the neural tube, opposite somites 20 and 21.

The cell suspension was inserted into a glass microcapillary tube and cells were deposited in each embryo using a pneumatic microinjector (Picopump PV830, World Precision Instruments).

The eggs were then returned to the 38.5° C. incubator for 48 hours.

Other Conditions

Several quantities of cancer cells grafted into an embryo were tested for performing the graft: 1,000 cells, 3,000 cells, 10,000 ($10^4$) cells and $5 \times 10^6$ cells.

Different stages of development of the recipient embryo were also tested for the time of the graft: stages HH10 (10 somites), HH1 (13 somites) and HH14 (22 somites).

Chick Embryo Sections

The embryos were harvested and fixed in 4% paraformaldehyde overnight at 4° C. Depending on the desired type of analysis, the embryos were cut to produce transverse and longitudinal sagittal sections. The sections were kept in PBS at 4° C. in the dark until use. Tumour location was studied by various labelling and/or fluorescence detection of the cancer cells previously transformed to express green fluorescent protein (GFP).

Labelling consists in incubating the cells in a vital fluorescent dye, CFSE, prior to the graft. Several concentrations of this vital dye were tested, allowing optimization of the detection of the tumour masses formed in the embryo after the graft.

Tumour Sampling In Situ and Analysis

The tumours are sampled by microdissection and subjected to various analyses:
  biochemical and transcriptomic studies (characterization and search for known or novel molecular markers), and
  in vitro studies via the reculturing thereof.

Image Capture and Processing

The sections were analysed using a confocal microscope (Olympus IX81). The complete image of the section was reconstituted using the XuvTools software.

Tumorigenesis was assessed by means of various analyses:
  Determination of the location of the tumour foci by histological analysis;
  Measurement of the tumour volume from the 3-dimensional reconstructed images;
  Determination of the proliferation index within the tumour foci by detection of marker Ki67;
  Determination of the vascularization index of the tumour foci by detection of markers of angiogenesis;
  Determination of the cell death index within the tumour foci by detection of cell death events (DNA fragmentation, necrosis, cytochrome c release, pro-apoptotic protease activation);
  Analysis of the transcriptome and of the proteome of the tumours extracted in situ;
  Study of the cell behaviour after reculturing.

The embryos were also analysed using a LaVision Biotec ultramicroscope. The embryos were scanned and the tumour recreated in 3D, allowing an analysis of volume and of anatomical location.

Results

According to the experimental protocol described above, human lung cancer (line A549), melanoma (line A375P), glioblastoma (line U251), medulloblastoma (line DEV) and breast cancer (line MDA MB 436) cells, expressing GFP or labelled with a vital dye, were grafted into a chick embryo at stage HH14. Further experiments were performed at earlier stages, HH10, HH11 and HH13.

The melanoma cells were grafted at the dorsal roof of the neural tube, between somites 18 and 24.

Forty-eight hours after the graft, the melanoma cells form tumour clusters subcutaneously and in the mesenchyme bordering the neural tube. (FIG. 4)

The glioblastoma and medulloblastoma cells were grafted onto a zone extending from the cervical neural crest (opposite somites 1 to 4) to the brain tissues bordering the cerebral ventricles of the various brain regions.

Forty-eight hours after the graft, the glioblastoma and medulloblastoma cells form tumour clusters in the brain and in the tissue bordering the cerebral ventricles. These tumours develop in the brain in a way comparable to the tumours observed in patients. (FIG. 5). The cancer cells migrate into the brain to establish new foci.

The lung cancer cells were grafted into the brain, at various locations in the brain regions. These cells were also grafted into the lateral mesenchyme opposite the vagal and trunk neural crests (somites 4 to 24).

Forty-eight hours after the graft, the lung cancer cells grafted at the somites form tumour clusters in the ventral horn of the neural tube and the adjacent lateral region thereof. (FIG. 6 and FIG. 7A). The cancer cells grafted into the brain tissues establish tumour masses in the brain, from which develop metastases that colonize new brain regions as well as more rostral regions of the embryo.

FIG. 7B shows the graft of lung tumour cells into zones covering the principal presumptive sites of human lung cancer metastases:
periorbital tissue,
first branchial arch,
hepatic anlage, and
limb anlage—sclerotome/dermamyotome.

The cells thus grafted form tumour clusters in the cartilage and the bones of the face (periorbital graft and graft into the first branchial arch), in the embryonic liver (graft into the hepatic anlage) and in the tissues deriving from the somites such as the bone tissue (graft into the sclerotome/dermamyotome). These grafts are referred to as 'heterotopic' since the tumours form in tissues different from those in which they originate.

The breast cancer cells were grafted into the brain, at various locations. Forty-eight hours after the graft, tumour clusters form in the brain tissues. A second focus of migration more rostral than the graft sites is present on the brain surface, in proximity to the skin layer (FIG. 8A).

The breast cancer cells were grafted into the brain of embryos at various stages of development: HH10, HH13 and HH14. Tumour foci were observed in the brain tissues on each grafted embryo, roughly 48 hours after the graft.

FIG. 8B shows the graft of mammary tumour cells into zones covering the principal presumptive sites of human mammary cancer metastases:
periorbital tissue,
first branchial arch,
hepatic anlage,
limb anlage—sclerotome/dermamyotome.

The grafted cells form tumour clusters in the cartilage and the bones of the face (periorbital graft and graft into the first branchial arch), in the embryonic liver (graft into the hepatic anlage) and in the tissues deriving from the somites such as the bone tissue (graft into the sclerotome/dermamyotome). These grafts are referred to as 'heterotopic' since the tumours form in tissues different from those in which they originate.

For each cancer cell type, several quantities of grafted cancer cells were tested, notably quantities of 1,000 cells, 3,000 cells and 10,000 cells per graft. Formations of tumours were observed at each of these concentrations, after 24 and 48 h of development of the grafted embryo in the egg after the graft.

REFERENCES

U.S. Pat. No. 6,228,345
WO 2015/074050
US 2013/0171680
Hamburger V., Hamilton H. L. *A series of normal stages in the development of the chick embryo*. J Morphol. 1951 January; 88(1):49-92.
Hagedom M, Javerzat S, Gilges D, Meyre A, de Lafarge B, Eichmann A, Bikfalvi A. *Accessing key steps of human tumor progression in vivo by using an avian embryo model*. Proc Natl Acad Sci USA. 2005 Feb. 1; 102(5): 1643-8.
Carter R, Mullassery D, See V, Theocharatos S, Pizer B, Losty P D, Jesudason E, Moss D J. *Exploitation of chick embryo environments to reprogram MYCN-amplified neuroblastoma cells to a benign phenotype, lacking detectable MYCN expression*. Oncogenesis. 2012 Aug. 27; 1:e24.
Kulesa P M, Kasemeier-Kulesa J C, Teddy J M, Margaryan N V, Seftor E A, Seftor R E, Hendrix M J. *Reprogramming metastatic melanoma cells to assume a neural crest cell-like phenotype in an embryonic microenvironment*. Proc Natl Acad Sci USA. 2006 Mar. 7; 103(10):3752-7. Epub 2006 Feb. 27.
Boulland J L, Halasi G, Kasumacic N, Glover J C. *Xenotransplantation of human stem cells into the chicken embryo*. J Vis Exp. 2010 Jul. 11; (41).

The invention claimed is:

1. A gallinaceous bird embryo for the study of cancer, comprising grafted human cancer cells that are not neuroblastoma cells, wherein:
said cancer cells are not grafted into the lumen of the neural tube,
said cancer cells are allowed to reproduce upon grafting at a developmental stage HH10 to HH25, and
said cancer cells form solid tumours in an implantation site within the gallinaceous bird embryo that is distinct from a grafting site.

2. The gallinaceous bird embryo of claim 1, wherein the gallinaceous bird embryo is at a developmental stage between stages HH12 and HH16 at the time of the graft, or between HH13 and HH15 at the time of the graft.

3. The gallinaceous bird embryo of claim 1, wherein the gallinaceous bird embryo is incubated for at least 24 hours after the graft.

4. The gallinaceous bird embryo of claim 1, wherein the cancer cells are grafted in a quantity of at least 1,000 cells per graft.

5. The gallinaceous bird embryo of claim 1, wherein the grafted cancer cells are labelled with a dye or express an exogenous marker protein.

6. The gallinaceous bird embryo of claim 1, wherein the cancer cells are grafted into the neural tube between somites 1 and 24 and/or into the brain tissues.

7. The gallinaceous bird embryo of claim 1, wherein the cancer cells are grafted into the brain tissues.

8. The gallinaceous bird embryo of claim 1, wherein the grafted cancer cells are selected from the group consisting of: melanoma cells, cells derived from primary or secondary brain tumours, lung cancer cells and breast cancer cells.

9. The gallinaceous bird embryo of claim 6, wherein the grafted cancer cells are melanoma cells, and are grafted into the dorsal roof of the neural tube or into the lateral proximity thereof, between somites 18 and 24.

10. The gallinaceous bird embryo of claim 6, wherein the grafted cancer cells are derived from primary or secondary brain tumours, and are grafted into the neural tube between somites 1 and 4, and/or into the brain tissues.

11. A process for preparing a gallinaceous bird embryo according to claim 1, comprising the following steps:
grafting of cancer cells that are not neuroblastoma cells within the tissues of a stage HH10 to HH25 gallinaceous bird embryo under suitable conditions allowing said cells to reproduce, wherein the cancer cells are not grafted into the lumen of the neural tube, and
incubating the grafted embryo for at least 24 hours, to form solid tumours in an implantation site within the gallinaceous bird embryo that is distinct from a grafting site.

12. A process for preparing tumours composed of cancer cells, comprising the process according to claim 11 and further comprising
sampling said tumours formed within the embryo.

13. The process of claim 12, wherein cancer cells are not melanoma cells.

14. The process according to claim 11, wherein the cancer cells are not melanoma cells.

15. The process of claim 11, wherein cancer cells are not melanoma cells.

16. The process of claim 11, wherein said cancer cells are from a tumour of a patient without any pre-culture.

17. The gallinaceous bird embryo of claim 1, wherein the cancer cells are not melanoma cells.

18. The gallinaceous bird embryo of claim 1, wherein the implantation site is located in tissues that are homologous to tissues from which the cancer cells were derived.

\* \* \* \* \*